(12) United States Patent
Wang et al.

(10) Patent No.: US 7,177,022 B2
(45) Date of Patent: Feb. 13, 2007

(54) METHOD AND SYSTEM REMOVING FLUORESCENCE AND OTHER SLOWLY VARYING BASELINE IN RAMAN SPECTRA

(75) Inventors: Xiaomie Wang, Winchester, MA (US); Xinfa Ma, Acton, MA (US)

(73) Assignee: Axsun Technologies, Inc., Billerica, MA (US)

( * ) Notice: Subject to any disclaimer, the term of this patent is extended or adjusted under 35 U.S.C. 154(b) by 0 days.

(21) Appl. No.: 11/357,896

(22) Filed: Feb. 17, 2006

(65) Prior Publication Data

US 2006/0197947 A1 Sep. 7, 2006

Related U.S. Application Data

(60) Provisional application No. 60/654,855, filed on Feb. 18, 2005.

(51) Int. Cl.
*G01J 3/44* (2006.01)
(52) U.S. Cl. ...................................................... 356/301
(58) Field of Classification Search ..................... None
See application file for complete search history.

(56) References Cited

U.S. PATENT DOCUMENTS

| | | | |
|---|---|---|---|
| 4,103,179 A | 7/1978 | Schmidt | |
| 5,194,912 A | 3/1993 | Batchedler et al. | |
| 5,257,085 A | 10/1993 | Ulich et al. | |
| 5,377,003 A | 12/1994 | Lewis et al. | |
| 5,384,589 A | 1/1995 | Ulich et al. | |
| 5,450,125 A | 9/1995 | Ulich et al. | |
| 5,532,998 A | 7/1996 | Durham | |
| 5,617,206 A | 4/1997 | Fay | |
| 5,946,090 A | 8/1999 | Tashiro et al. | |
| 6,002,476 A | 12/1999 | Treado | |
| 6,181,957 B1 | 1/2001 | Lambert et al. | |
| 6,567,678 B1 | 5/2003 | Oosta et al. | |
| 6,574,501 B2 | 6/2003 | Lambert et al. | |
| 6,583,873 B1 | 6/2003 | Goncharov et al. | |
| 6,690,509 B2 | 2/2004 | Vodyanoy et al. | |
| 6,717,688 B1 | 4/2004 | Treado et al. | |
| 6,731,423 B1 | 5/2004 | Brasseur et al. | |
| 6,765,668 B2 | 7/2004 | Gardner, Jr. et al. | |
| 6,813,429 B2 | 11/2004 | Price et al. | |
| 2001/0052979 A1 | 12/2001 | Treado et al. | |
| 2002/0135871 A1 | 9/2002 | Vodyanoy et al. | |
| 2002/0168161 A1 | 11/2002 | Price et al. | |
| 2003/0004419 A1 | 1/2003 | Treado et al. | |
| 2003/0018272 A1 | 1/2003 | Treado et al. | |

(Continued)

FOREIGN PATENT DOCUMENTS

EP 0 404 901 B1 1/1991

(Continued)

*Primary Examiner*—Tu T. Nguyen
(74) *Attorney, Agent, or Firm*—Houston Eliseeva LLP

(57) ABSTRACT

A data set processing method for Raman spectroscopy systems using tunable lasers and multielement spectrometers compiles the spectral data set into an array and then estimates the background component, which is usually dominated by sample and optical train fluorescence, detector array dark current signal, fixed-pattern signal, and stray-light signals either modulated or non-modulated by in-path optics. This estimate is used as a baseline correction to the spectral data set to thereby isolate the sample's Raman response.

15 Claims, 2 Drawing Sheets

U.S. PATENT DOCUMENTS

| | | |
|---|---|---|
| 2003/0023152 A1 * | 1/2003 | Abbink et al. ............... 600/316 |
| 2003/0023170 A1 * | 1/2003 | Gardner et al. ............. 600/476 |
| 2003/0043451 A1 | 3/2003 | Kato et al. |
| 2004/0008522 A1 | 1/2004 | Vodyanoy et al. |
| 2004/0019283 A1 | 1/2004 | Lambert et al. |
| 2004/0021860 A1 | 2/2004 | Gardner, Jr. et al. |
| 2004/0090669 A1 | 5/2004 | Vodyanoy et al. |
| 2004/0096981 A1 | 5/2004 | Weimer |
| 2004/0127778 A1 | 7/2004 | Lambert et al. |
| 2004/0169854 A1 | 9/2004 | Vo-Dinh et al. |
| 2004/0189989 A1 | 9/2004 | Gardner, Jr. et al. |
| 2005/0248758 A1 | 11/2005 | Carron et al. |

FOREIGN PATENT DOCUMENTS

| | | |
|---|---|---|
| EP | 0 474 264 A2 | 3/1992 |
| EP | 0 543 578 A1 | 5/1993 |
| EP | 0 638 788 A1 | 2/1995 |
| EP | 1 288 705 A2 | 3/2003 |
| WO | WO 90/07108 A1 | 6/1990 |
| WO | WO 96/25735 A1 | 8/1996 |
| WO | WO 97/21079 A1 | 6/1997 |
| WO | WO 00/02479 A1 | 1/2000 |
| WO | WO 02/27287 A1 | 4/2002 |
| WO | WO 02/060321 A2 | 8/2002 |
| WO | WO 02/061485 A2 | 8/2002 |
| WO | WO 02/084821 A2 | 10/2002 |
| WO | WO 03/060444 A1 | 7/2003 |
| WO | WO 2004/064969 A1 | 8/2004 |
| WO | WO 2004/079351 A1 | 9/2004 |
| WO | WO 2004/086939 A2 | 10/2004 |

* cited by examiner

METHOD AND SYSTEM REMOVING FLUORESCENCE AND OTHER SLOWLY VARYING BASELINE IN RAMAN SPECTRA

RELATED APPLICATIONS

This application claims the benefit under 35 USC 119(e) of U.S. Provisional Application No. 60/654,855, filed on Feb. 18, 2005, which is incorporated herein by reference in its entirety.

BACKGROUND OF THE INVENTION

Raman spectroscopy is similar to infrared (IR), including near infrared (NIR), spectroscopy but has several advantages. The Raman effect is highly sensitive to slight differences in chemical composition and crystallographic structure. These characteristics make it very useful for substance identification such as the investigation of illegal drugs and other unknown substances as it enables distinguishing between legal and illicit compounds, even when the compounds have a similar elemental composition. In other applications, taggants, with known Raman signatures, are used as markers for goods.

Raman spectroscopy has additional advantages. When using IR spectroscopy on aqueous samples, a large proportion of the vibrational spectrum can be masked by the intense water signal or absorbed by the water. This typically necessitates sample preparation. In contrast, with Raman spectroscopy, aqueous samples can be more readily analyzed since the Raman signature from water is relatively weak. Also, because of the poor water signature, Raman spectroscopy is often useful when analyzing biological and inorganic systems, and in studies dealing with water pollution problems.

Raman scattering may be regarded as an inelastic collision of an incident photon with a molecule. The photon may be scattered elastically, that is without any change in its wavelength, and this is known as Rayleigh scattering. Conversely the photon may be scattered inelastically resulting in the Raman effect.

There are two types of Raman transitions. Upon collision with a molecule, a photon may lose some of its energy. This is known as Stokes radiation. Or, the photon may gain some energy—this is known as anti-Stokes radiation. This happens when the incident photon is scattered by a vibrationally excited molecule—there is gain in energy and the scattered photon has a higher frequency.

When viewed with a spectrometer, both the Stokes and anti-Stokes radiation are composed of lines that correspond to molecular vibrations of the substance under investigation. Each compound has its own unique Raman spectrum, which can be used as a fingerprint for identification.

The Raman process is non linear. When incident photons have a low intensity, only spontaneous Raman scattering will occur. As the intensity of the incident light wave is increased, an enhancement of the scattered Raman field can occur in which initially scattered Stokes photons can promote further scattering of additional incident photons. With this process, the Stokes field grows exponentially and is known as stimulated Raman scattering (SRS).

One disadvantage associated with Raman spectroscopy, however, is fluorescence Fluorescence arising from molecular relaxation radiation has been the major obstacle for Raman spectroscopy. In many cases, the fluorescence response of a sample can overwhelm the typically much weaker Raman signature. This can make detection of small peaks in the Raman signature difficult. Some data processing techniques to the fluorescence baseline corrections are not effective since they usually do not provide sufficient discrimination between the fluorescent baseline and the Raman spectra.

Often, fluorescence can be mitigated by moving to a longer wavelength excitation. This can create other problems, however. Another solution to the fluorescence response is using excitation signals at multiple wavelengths. This is sometimes referred to as Shifted Excitation Raman Difference Spectroscopy (SERDS). Specifically, in the past others have suggested to use excitation signals that comprise two excitation wavelengths, generated by two different single frequency lasers. Then, by looking at the spectra generated by each of the wavelengths, the fluorescence signal can be identified since the fluorescence signal changes very little with excitation wavelength, whereas the Raman signal changes as a direct function of the excitation wavelength. In the simplest example, the spectrum at the two wavelengths is subtracted to remove the highly stationary fluorescence response. Recently, this solution has been further enhanced by using a continuously tunable semiconductor diode laser system. In these systems, the spectral response of the sample is monitored as the excitation signals wavelength is scanned over a scan range. By looking at how the spectral response changes with the tuning of the excitation signal and how it does not change, the Raman response can be separated from the fluorescence response of the sample.

SUMMARY OF THE INVENTION

Using a continuously tunable or a small step-wise tunable laser source in combination with a multi element detector system such as a grating-based spectrometer with a linear detector array, yields a large spectral data set compromised of each detector elements sampled response at each wavelength in the tunable laser's scan range. This spectral data set must be processed to remove noise, such as the fluorescence response and thereby isolate the Raman response.

The present invention concerns a data set processing method for Raman spectroscopy systems using tunable lasers and multielement spectrometers. One example of such a spectrometer is the conventional grating-based dispersive spectrometer in which a grating is used to disperse the spectrum onto a linear detector array. Other examples are the tunable multiorder multichannel Raman spectrometers described in U.S. patent application Ser. No. 10/967,075, filed Oct. 15, 2004, by Xiaomei Wang, entitled Multi Channel Raman Spectrometer System and Method, which application is incorporated herein in its entirety by this reference.

The invention comprises compiling the spectral data set into an array and then estimating the background component, which is usually dominated by sample and optical train fluorescence, detector array dark current signal, fixed-pattern signal, and stray-light signals either modulated or non-modulated by in-path optics. This estimate is used as a baseline correction to the spectral data set to thereby isolate the sample's Raman response.

In principle, the invention is applicable in any tunable laser based Raman spectrometers, where fluorescence is present. By effectively removing the fluorescence and any other non-Raman background, the processed spectrum reflects the true substance properties. This produces much higher identification fidelity when identifying the substances against libraries.

The theory behind this invention is that the spectra of fluorescence and some other baseline background, such as sample heat radiation, are described in absolute wavelength (frequency) domain, and fully characterized by the detection wavelength only. They usually have much broader peaks than Raman spectral peaks. The Raman spectra, on the other hand, depend on the Raman shift, which is related to both excitation and detection wavelength.

In general, according to one aspect, the invention features a method of processing spectral data from a Raman spectroscopy system. This spectroscopy system comprises a source for illuminating a sample at a plurality of wavelengths within a scan band. In one example, the source is a tunable laser. A spectrometer is also provided. It includes an array of detection elements. One example is a linear detector array such as a CCD or InGaAs type detector arrays. The array detects the spectral response of the sample as the source is illuminated at the plurality of wavelengths. The method comprises compiling a spectral data set including the responses of the detection elements for each of the plurality of wavelengths. The responses are then characterized based on levels of change in the response with changes in the wavelength of the illumination. Then, a baseline is determined from the responses, and the spectral data set is corrected using the determined baseline.

In specific embodiments, the spectrometer comprises a dispersive element such as a grating for dispersing the spectral response over the array of detection elements. In further examples, the step of compiling the spectral data set comprises placing the spectral data set in an array of responses for each of the detection elements for each of the plurality of wavelengths. The step of characterizing responses comprising analyzing responses of each of the detection elements with changes in the wavelength of illumination. One method of characterizing these changes is to calculate a standard deviation in the responses with changes and wavelength.

The baseline is then determined typically by excluding the responses of the detection elements that exhibit a large change in standard deviation. A best fit polynomial is used in one example to characterize the baseline. This baseline is then subtracted from the spectral data set.

In general, according to another aspect, the invention features a Raman spectroscopy system. This system comprises a source for illuminating a sample at a plurality of wavelengths within a scan band. A spectrometer includes an array of detection elements for detecting a spectral response of the sample in response to illumination by the source at the plurality of wavelengths. A system controller controls the source and receives the responses from the detection elements of the spectrometer. The system controller processes the spectral data to determine a Raman response of the sample. This is accomplished by compiling a spectral data set including the responses of the detection elements for each of the plurality of wavelengths and characterizing the responses of the detection elements based on levels of change in the response with changes in the wavelength of the illumination. Based on this analysis, a baseline is determined for the responses, and the spectral data set is then corrected based on the response to the determined baseline.

The above and other features of the invention including various novel details of construction and combinations of parts, and other advantages, will now be more particularly described with reference to the accompanying drawings and pointed out in the claims. It will be understood that the particular method and device embodying the invention are shown by way of illustration and not as a limitation of the invention. The principles and features of this invention may be employed in various and numerous embodiments without departing from the scope of the invention.

BRIEF DESCRIPTION OF THE DRAWINGS

In the accompanying drawings, reference characters refer to the same parts throughout the different views. The drawings are not necessarily to scale; emphasis has instead been placed upon illustrating the principles of the invention. Of the drawings.

DETAILED DESCRIPTION OF THE PREFERRED EMBODIMENTS

Figure 1:
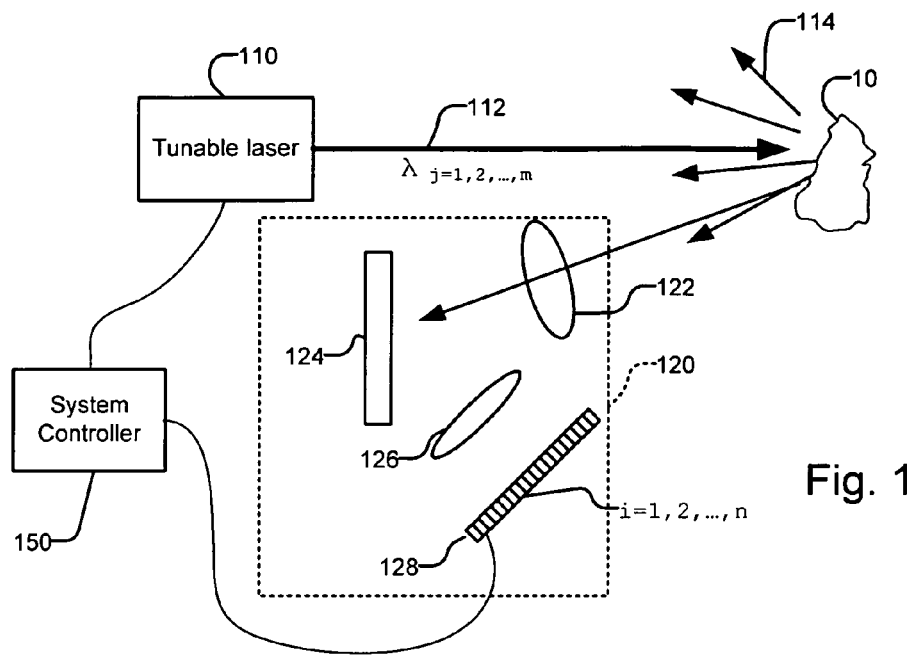
FIG. 1 is a schematic diagram illustrating a Raman spectroscopy system to which the present invention is applicable.

FIG. 1 illustrates a spectroscopy system to which the present invention is applicable. Specifically, it comprises a source 110 for generating a tunable wavelength illuminating beam 112 for irradiating the sample 10 at a plurality of wavelengths $\lambda_1$, $\lambda_2$, $\lambda_m$. Typically, the source 100 is a tunable laser.

The illumination of the sample 110 by the laser beam 112 generates a response 114. Typically this response is a combination of the fluorescence response and the Raman response of the sample 10.

In order to resolve the spectral response of the sample 10, a spectrometer 120 is used. As a general example, the spectrometer comprises collection optics 122 that collect light from the sample 10 and direct it to a dispersive element 124. In the typical example, the dispersive element 124 is a grating such as a standard line grating or a holographic grating.

The dispersive element 124 disperses the spectrum of the light 114 from the sample 10 in order to determine the spectral response of the sample 10. In the specific example, grating optics 126 is used to form the spectral image on the linear detector array 128. In the preferred embodiment, this is a linear detector array 128 comprises elements i=1, 2, ... n. Often n is greater than 10 and typically greater than 32.

A system controller 150 is used to control the tunable laser 110 and specifically control its wavelength $\lambda$. The system controller 150 also receives the responses of the detection elements i=1, 2, ... n from the detector array 128.

According to the present invention, the system controller analyzes the spectral data from the detector array 128 in combination with the wavelength of the tunable laser 110 in order to determine the Raman spectral response of the sample 10.

Figure 2:
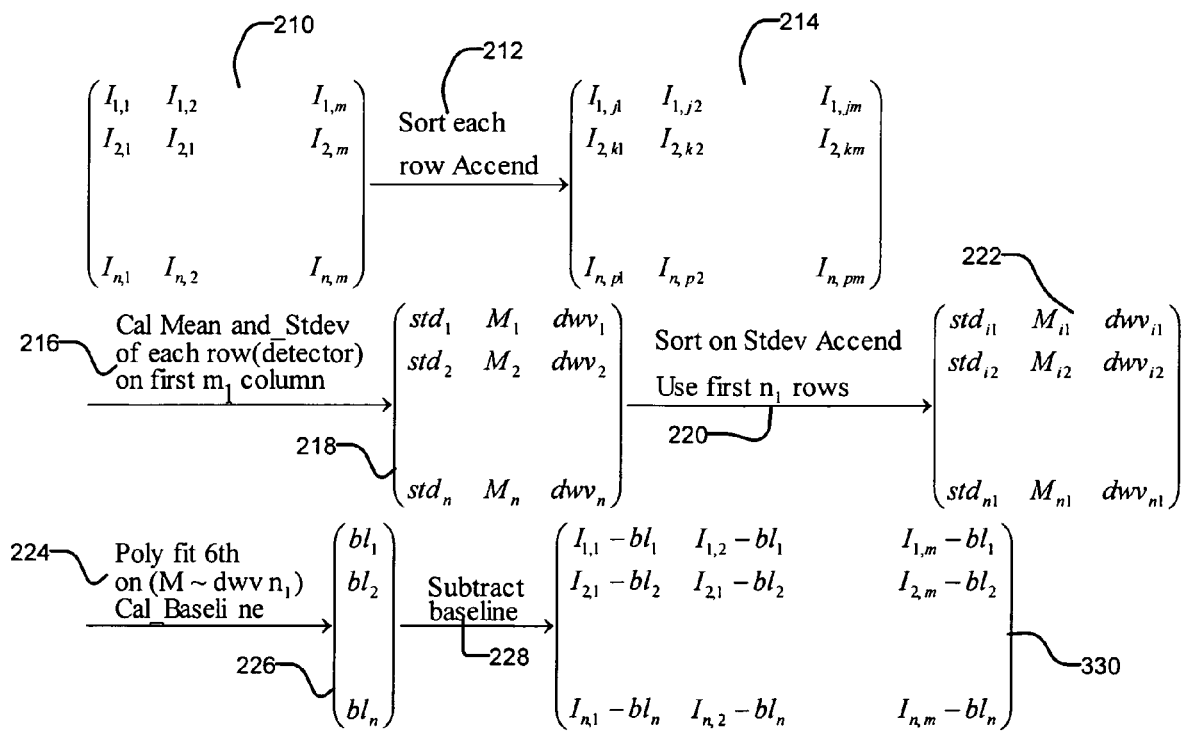
FIG. 2 is a flow diagram illustrating a method for processing a spectral data from a Raman spectroscopy system.

FIG. 2 shows the baseline estimation method according to the principles of the present invention.

The detected signal at the detector array 128 can be written as: $Iij = Ii(fluorescence) + Ii(dark\ current) + Ii(sample\ heating) + Iij(Raman\ signal)$, where i=1,2, ... , n, represents each detector and j=1, 2, ..., m, each step wise tuning point of the laser 110 or data acquisition point in a continuously tuning mode of the laser.

In one example, the scan band of the laser 110 is between 1 and 15 nanometers. In a preferred embodiment, the scan band is between 2 and 5 nanometers. The spectral responses of the detector array 128 are collected at more than 5 different wavelengths (m>5) within the scan band. In the preferred embodiment, spectral responses of the detector array 128 are collected at more than 12, preferably more than 20, different wavelengths within the scan band.

The responses of the detection elements at each of the wavelengths $\lambda_1 \ldots \lambda_m$ are compiled into a spectral data set 210. Specifically, the spectral data set 210 is formed into an array of responses that holds each of the detection elements response for each of the plurality of wavelengths.

Then, in step 212, the original spectral data set 210 is sorted so that the detected responses are in ascending order for each detector individually. It produces a sorted array 214.

From the sorted array, the mean and standard deviation are calculated for each of the detectors i=1 to n in step 216. In the current embodiment, this is performed for a selected number m1 of data points or a number of data points determined by a user selected criterion for each detector. This criterion can be either fixed or dynamically variable based on the data set. This process produces an array of calculated mean and standard deviation values 218.

In step 220, the standard deviation and mean array 218 is sorted and only a fixed number n1 or a number of detectors with the standard deviation less than a threshold times the lowest standard deviation, among the detectors, are selected to produce array 222. In short, the responses of the detector elements that exhibited the smaller changes, have lower standard deviation as a function of changes in wavelength, are identified. The responses of these detector elements that exhibited the lowest change are then used to calculate a polynomial fit as a function of detector wavelengths in step 224. This produces a polynomial array 226.

In one embodiment, the fitting results are analyzed and any outliers are removed. The polynomials are refit and the baseline is then re-calculated. This produces the polynomial array 226. This baseline is then subtracted in step 228. This produces the corrected Raman spectral response array 330.

Figure 3:
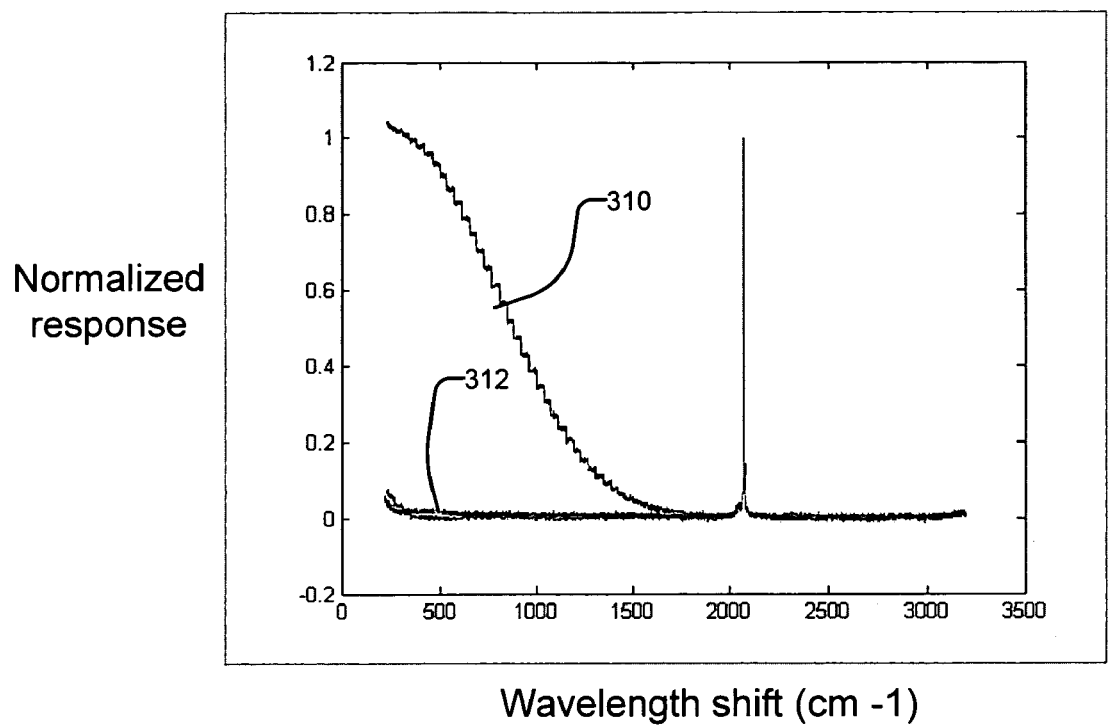
FIG. 3 is plot of normalized response as a function of shift in wavenumbers (cm −1) for a Raman spectrum of potassium cyanide (KCN) with a Gaussian-like fluorescence baseline.

Simulations of the method's performance were performed with four different slow varying baselines: linear, parabolic, slow and fast Gaussian. Due to the nature of the multiorder multichannel detection of the tunable multiorder multichannel Raman spectrometers as described in U.S. patent application Ser. No. 10/967,075, a typical expected detected signal with fluorescent baseline is illustrated in FIG. 3, where the Raman spectrum is from Potassium Cyanide and the baseline 310 is assumed to be in a fast Gaussian form. A stair-like baseline presents the discrimination between Raman signal and fluorescence background.

In the simulation, we used the following parameters:

1. Number of detectors: n=64
2. Number of tuning steps: m=41
3. Number of data points used for standard deviation and calculation: m1=10
4. Number of detectors used for baseline estimation: n1=30

Reference 312 illustrated the baseline corrected response of KCN with a single peak.

Figure 4:
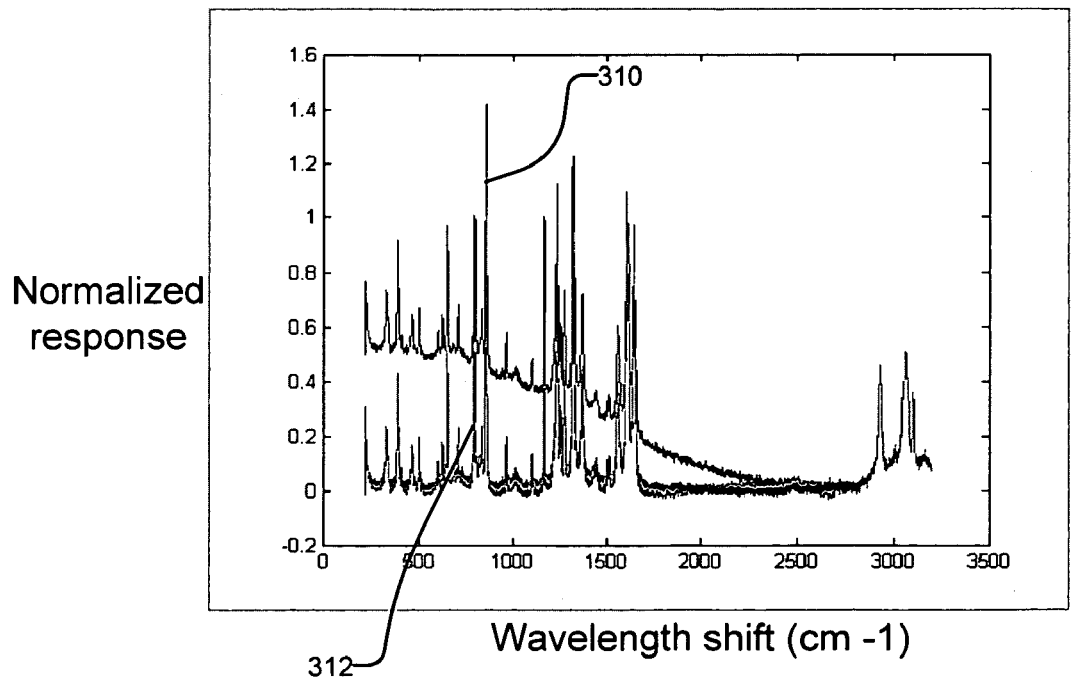
FIG. 4 is plot of normalized response as a function of shift in wavenumbers (cm −1) for a Raman spectrum of acetaminophen.

FIG. 4 shows the raw response 310 and the baseline corrected Raman response 312 for over-the-counter acetaminophen.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of processing spectral data from a Raman spectroscopy system, comprising:
   a source for illuminating a sample at a plurality of wavelengths within a scan band; and
   a spectrometer including an array of detection elements for detecting a spectral response of the sample in response to illumination by the source at the plurality of wavelengths;
   wherein the method comprises:
      compiling a spectral data set including the responses of the detection elements for each of the plurality of wavelengths;
      characterizing the responses of the detection elements based on levels of change in the responses with changes in the wavelength of the illumination;
      determining a baseline from the responses; and
      correcting the spectral data set using the determined baseline.

2. A method as claimed in claim 1, wherein the spectrometer of the Raman spectroscopy system further comprises a dispersive element of dispersing the spectral response over the array of detection elements.

3. A method as claimed in claim 1, wherein the step of compiling the spectral data set comprises placing the spectral data set in an array of responses for each of the detection elements for each of the plurality of wavelengths.

4. A method as claimed in claim 1, wherein the step of characterizing the responses comprises analyzing the responses of each detection elements for changes with changes in the wavelength of the illumination.

5. A method as claimed in claim 1, wherein the step of characterizing the responses comprises analyzing the responses of each detection element based on the deviation in the responses with changes in the wavelength of the illumination.

6. A method as claimed in claim 1, wherein the step of determining the baseline comprising determining a best fit polynomial.

7. A method as claimed in claim 1, wherein the step of correcting the spectral data set comprises subtracting the baseline from the spectral data set.

8. A Raman spectroscopy system, comprising:
   a source for illuminating a sample at a plurality of wavelengths within a scan band;
   a spectrometer including an array of detection elements for detecting a spectral response of the sample in response to illumination by the source at the plurality of wavelengths; and
   a system controller for controlling the source and receiving responses of the detection elements of the spectrometer, the system controller processing the spectral data to determine a Raman response of the sample by compiling a spectral data set including the responses of detection elements for each of the plurality of wavelengths, characterizing the responses of the detection elements based on levels of change in the responses with changes in the wavelength of the illumination, determining a baseline from the responses, and correcting the spectral data set in response to the determined baseline.

9. A system as claimed in claim 8, wherein the spectrometer of the Raman spectroscopy system further comprises a dispersive element of dispersing the spectral response over the array of detection elements.

10. A system as claimed in claim 8, wherein the source comprises a tunable laser.

11. A system as claimed in claim 8, wherein the system controller compiles the spectral data set by placing the spectral data set in an array with responses for each of the detection elements for each of the plurality of wavelengths.

12. A system as claimed in claim 8, wherein the system controller characterizes the responses by analyzing the responses of each detection element for changes with changes in the wavelength of the illumination.

13. A system as claimed in claim 8, wherein the system controller characterizes the responses by analyzing the responses of each detection element based on the deviation in the responses with changes in the wavelength of the illumination.

14. A system as claimed in claim 8, wherein the system controller determines the baseline by determining a best fit polynomial.

15. A system as claimed in claim 8, wherein the step of correcting the spectral data set comprises subtracting the baseline from the spectral data set.

* * * * *

UNITED STATES PATENT AND TRADEMARK OFFICE
CERTIFICATE OF CORRECTION

PATENT NO. : 7,177,022 B2
APPLICATION NO. : 11/357896
DATED : February 13, 2007
INVENTOR(S) : Xiaomei Wang and Xinfa Ma It is certified that error appears in the above-identified patent and that said Letters Patent is hereby corrected as shown below:

On page 1, Paragraph (75) Inventors, delete "Xiaomie" and insert --Xiaomei--.

Signed and Sealed this

Tenth Day of April, 2007

JON W. DUDAS
*Director of the United States Patent and Trademark Office*